United States Patent [19]

Soll et al.

[11] Patent Number: 5,006,123
[45] Date of Patent: Apr. 9, 1991

[54] SCLERA AND/OR LIMBUS MARKING DEVICE FOR USE IN INTRAOCULAR SURGERY

[76] Inventors: David B. Soll, 5001 Frankford Ave., Philadelphia, Pa. 19124; Stephen J. Failla, 39 Dogwood Dr., Chester, N.J. 07930

[21] Appl. No.: 404,146

[22] Filed: Sep. 7, 1989

Related U.S. Application Data

[62] Division of Ser. No. 177,716, Apr. 5, 1988, Pat. No. 4,880,017.

[51] Int. Cl.⁵ .............................................. A61F 9/00
[52] U.S. Cl. ..................................... 606/166; 33/512
[58] Field of Search ............... 606/161, 166, 184, 185, 606/107; 101/327, 368, 371, 372, 379, 405; 33/512, 669, 19.3

[56] References Cited

U.S. PATENT DOCUMENTS

| | | |
|---|---|---|
| 345,064 | 7/1886 | Lidke .................................... 101/371 |
| 2,839,994 | 6/1958 | Haag ..................................... 101/372 |
| 2,932,296 | 4/1960 | Sanders . |
| 3,074,407 | 1/1963 | Moon et al. . |
| 3,502,070 | 3/1970 | Bliss . |
| 3,951,062 | 4/1976 | Abramson . |
| 4,192,312 | 3/1980 | Wilson . |
| 4,238,161 | 12/1980 | Morohashi . |
| 4,336,805 | 6/1982 | Smirmaul . |
| 4,357,941 | 11/1982 | Golubkov et al. . |
| 4,406,285 | 9/1983 | Villasenor . |
| 4,417,579 | 11/1983 | Soloviev et al. . |
| 4,440,168 | 4/1984 | Warren . |
| 4,515,157 | 5/1985 | Fedorov et al. . |
| 4,542,742 | 9/1985 | Winkelman et al. . |
| 4,576,163 | 3/1986 | Bliss . |
| 4,739,761 | 4/1988 | Grandon . |

OTHER PUBLICATIONS

Letter dated May 16, 1989 from John A. Artz, Esq. to Alan S. Nadel, Esq.
Brochure entitled "Storz Presents Instruments Designed by Dr. Spencer P. Thornton," bearing a 1987 copyright notice in the name of Storz Instrument Company.
Copy of an advertising literatire appropriation request dated Sep. 18, 1987.
Copy of a purchase order for the brochure dated Oct. 22, 1987.

*Primary Examiner*—C. Fred Rosenbaum
*Assistant Examiner*—William W. Lewis
*Attorney, Agent, or Firm*—Panitch, Schwarze, Jacobs & Nadel

[57] ABSTRACT

A marking device is provided for marking the sclera and/or limbus of a patient's eye to standardize and define incision location and suture placement prior to cataract removal, and to aid in the intraoperative control of astigmatism. The device comprises a generally arcuate body member having opposed major surfaces with a plurality of projections extending from one of the major surfaces. The body member has an inferior arc and a superior arc with the inferior arc having a smaller radius than the superior arc. The projections are radially aligned, extending from the major surface and are adapted to be inked and to transfer ink marks to the sclera and/or limbal area of an eye. The ink marks represent the locations where incisions and sutures are to be placed.

28 Claims, 2 Drawing Sheets

SCLERA AND/OR LIMBUS MARKING DEVICE FOR USE IN INTRAOCULAR SURGERY

CROSS REFERENCE TO RELATED APPLICATION

This is a division of U.S. patent application Ser. No. 177,716, filed Apr. 5, 1989.

FIELD OF THE INVENTION

The present invention generally relates to a suture and/or incision marking device for placing ink markings on the sclera and/or limbal area of a patient's eye. Additionally, the invention relates to a method for placing ink markings on the sclera and/or limbal area of a patient's eye prior to cataract or intraocular surgery in order to standardize and define the location and length of the incision and suture placement.

BACKGROUND OF THE INVENTION

Intraocular lens surgical procedures, and specifically cataract surgery to which the present invention is directed primarily, have become more sophisticated, with less intraoperative complications occurring. Hence, ophthalmologists now are focusing more attention on the refinements, one of which is the correction and prevention of corneal astigmatism. In order for the surgeon to be able to properly evaluate the effects of their cataract incisions and closures, several requirements are necessary.

The incision must be as standardized and reproducible as possible, as should be the closure, including the number and type of sutures, the suture material and the placement of sutures and their corresponding knots. The suture tension should also be adjustable according to the individual surgical requirements. The sclera and/or limbal marker and method of using it in intraocular surgery according to the present invention are effective in refining the intraocular surgical techniques required in procedures such as cataract removal and intraocular lens implantation. The use herein of the terms "sclera and/or limbus" and "sclera and/or limbal area" with respect to procedures involving the use of the present invention relate to the personal preferences of surgeons as to the location of making incisions for this type of surgery as opposed to corneal surgery. Thus, in some procedures, a surgeon may wish to mark the sclera and in others, the limbus or limbal area which defines the boundary region between the cornea and the sclera.

Final astigmatism correction, at the time of closure, may be monitored by any one of a number of available hand-held or microscope-mounted surgical keratometers, or may merely be estimated by the surgeon.

Various types of instruments have been used to aid in standardizing incisions in the cornea during radial and non-radial keratotomy ophthalmosurgery for the control of astigmatism. However, prior to the present invention, no one has devised a sclera and/or limbal marker and method of using it for other types of ophthalmosurgery. One device comprises a case in the form of a bush having a central opening to accommodate a sight centering means, and a series of plates at right angles to the sight centering means. The plates are adapted to be brought into contact with the cornea to be marked out. The plates are provided with sharpened curvilinear edges corresponding to the curvature of the cornea. In use, the plates of the device are pressed into the eye to cause temporary elastic deformation or indentations of the cornea to mark areas for incising the cornea.

A similar marking device has the same basic structure as the prior art device described above, except that each plate is mounted on a separate holder for adjustable movement radially with respect to the bush. The sharp bladed tips of the plates cause corneal indentations when pressed against the eye. The eye may be pre-stained with brilliant green dye prior to pressing the plates of the blades onto the eye.

These devices, however, mark the cornea of a patient's eye and are used in radial keratotomy or corneal transplants. Their purpose is to make radial marks for radial incisions on the cornea in order to help reduce myopia. Non-radial incisions or combinations of non-radial and radial incisions on the cornea are used to reduce postoperative astigmatism and/or myopia associated with corneal surgery.

Other devices are known for use as blanks or templates against a patient's skin to define the proper incision pattern to promote proper handling with a hairline scar. One of these devices is a skin biopsy device which includes a plurality of short members extending outwardly from the template sides. The members act as markers to indicate the location of sutures when the device is pressed against the skin to make the skin red or discolored in the area of the marker members.

A problem encountered in using ophthalmosurgical or skin marking devices of the prior art is that they are not adapted for use in cataract surgery to mark the sclera and/or limbus of an eye to indicate the location of sutures instead of or in addition to incisions. Furthermore, due to their sharp edges, the ophthalmosurgical marker devices are designed to mark the cornea of an eye, prior to corneal surgery, by indenting the corneal surface. Cataract surgery on the other hand, requires the marking of the sclera and/or limbal area. The incision used in cataract and/or intraocular lens surgery is made perpendicular to the marking lines of the present invention and not parallel to the marking lines as described in the prior art. The marking lines are also used for suture placement after the incision is made. The skin marking devices are also not adapted for use in any way in cataract surgery.

Some surgeons presently use ink to mark the sclera prior to making the incision. They use ink-dipped dividers preset to the desired dimensions. Depending on the desired dimensions, this may require the use of more than one set of dividers, the dividers have to be carefully aligned in each instance, and, because of the extra care and manipulation required, the procedure is rather time consuming.

The present invention provides an incision and/or suture marking device having a plurality of precisely oriented, outwardly extending projections coated with a waterproof ink, such as gentian violet, which when pressed gently onto a patient's eye places ink markings on the sclera and/or limbal areas after the conjunctiva is "reflected" (cut and folded back, usually distally, to form a "fornix based flap"), indicating the length and location where incisions and sutures are to be placed during surgery. The inked projections make ink marks which will define the proper length bites for a suture needle on either side of an incision line during suture placement. By indicating the placement of sutures on the sclera and/or limbus, rather than merely the location of incisions on the cornea as in the ophthalmosurgical devices of the prior art, surgeon induced astigmatism often resulting from tangential displacement of tissue at the incision line caused by uneven or improper suture placement after cataract removal can be controlled or eliminated. Furthermore, where pre-existing astigmatism exists, the skilled cataract surgeon can reduce or even eliminate it by judicious placement of the cataract incision, and/or varying the suture tension.

The marking device, when pressed onto the sclera and/or limbus of any eye prior to surgery, among other things: defines the length and location of incisions and suture placement by making predetermined patterns of ink marks on the scleral and/or limbal areas of the eye; provides for proper, and preferably equal, spacing between sutures; defines uniform suture bites, for example 1 mm or other desired dimensions, on each side of the incision; and allows the surgeon to accurately reappose the proximal and distal sides of the incision without lateral displacement along the incision line. These in turn prevent misalignment of wound surfaces during suture placement, thus reducing or eliminating the possibility of postoperative astigmatism.

SUMMARY OF THE INVENTION

One aspect of the present invention relates to a marking device for marking a sclera and/or limbal portion of an eye during intraocular surgery comprising a generally arcuate body member having opposed first and second major surfaces, a plurality of projections extending from the first major surface, the projections being generally equiangularly spaced from each other and radially arranged in a pattern along an arc of a circle, the projections being adapted to be inked and to transfer to an eye the ink in markings corresponding to the projections so that incisions and sutures can be placed in the sclera and/or limbal portion of the eye relative to the markings.

Another aspect of the present invention relates to a method for marking the sclera and/or limbal portion of an eye prior to intraocular surgery to help control and prevent postoperative astigmatism using a marking device wherein the marking device comprises a generally arcuate body member having opposed first and second major surfaces, and a plurality of projections extending from the first major surface, the projections being generally equiangularly spaced from each other and radially arranged in a pattern along the arc of a circle, the method comprising reflecting the conjunctiva of the eye so as to expose the sclera and/or limbus of the eye, coating waterproof ink onto the projections of the device, pressing the device onto the sclera and/or limbus with sufficient pressure to transfer ink from the projections onto the sclera and/or limbus to create ink markings corresponding to the projections, and removing the device from the eye.

BRIEF DESCRIPTION OF THE DRAWINGS

The foregoing summary, as well as the following detailed description of a preferred embodiment of the invention, will be better understood when read in conjunction with the appended drawings, in which.

DETAILED DESCRIPTION OF THE PREFERRED EMBODIMENTS

Figure 1:
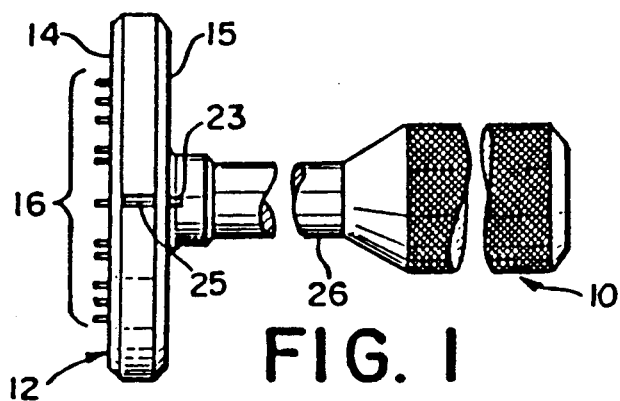
FIG. 1 is a side elevational view of a first embodiment of a marking device according to the present invention showing projections extending from a first, planar major surface of the arcuate body member.
Figure 2:
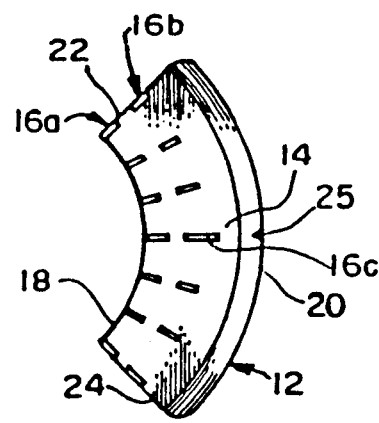
FIG. 2 is a side elevational view of the embodiment of FIG. 1 taken from the left side of FIG. 1.

Referring to the drawings in detail, where like numerals indicate like elements throughout the several views, there is shown in FIGS. 1 and 2 a first embodiment of a marking device 10 in accordance with the present invention.

The marking device 10 of the present invention, generally made of a corrosion-resistant material such as plastic or stainless steel, comprises a generally arcuate body member 12 having a first, planar major surface 14 and an opposed, second planar major surface 15 with a plurality of projections 16 extending from the first major surface 14. The arcuate body member 12 comprises an inferior arc 18 and a superior arc 20 joined by end edges 22 and 24, the inferior arc 18 having a smaller radius than the superior arc 20. In the presently preferred embodiment, the body member 12 covers approximately 40 to about 160 degrees of a circle, and most preferably, about 90 degrees. The inferior arc 18 preferably has a radius of curvature equal to the average person's limbal or corneal radius of curvature, which is approximately 6 mm. The superior arc 20 preferably has a radius of curvature of 10 to 11 mm. It should be understood, however, that the radii of curvature of the body member 12 may vary, depending on the surgeon's choice of incision and suture locations relative to the limbus.

In the first embodiment, as best seen in FIG. 2, the projections 16 extend radially from the inferior arc 18 in a direction toward the superior arc 20 and are in a pattern along an arc of a circle, equiangularly spaced from each other. Although the projections 16 are illustrated in FIG. 2 as having generally rectangular blunt faces or tips which extend in a direction from the inferior arc 18 toward the superior arc 20, the projections can be of any desired shape, such as dots, circles, +'s, X's, or the like as desired. The blunt tips of the projections are adapted to be inked and leave marks of waterproof ink on the sclera and/or limbus which are easy for a surgeon to see and use to make an eye incision and suture it properly.

In the first embodiment, the projections 16 are arranged in two sets 16a and 16b of a like or different number, such as seven in each set in the presently preferred embodiment. The first set 16a of radial projections is located along the inferior arc 18. The second set of projections 16b are preferably radially aligned with and equidistantly spaced from the first set 16a, although, if desired, the second set could be aligned along a predetermined arc of a different, non-parallel radius. A central projection in at least one set, such as central projection 16c should have a distinguishing characteristic to help the surgeon to discern the center of the incision. As best illustrated in FIG. 2, the central projection 16c is longer than the other projections.

It should be understood that any other suitable number, shape, arrangement or spacing of projections 16 may be employed, depending on the number of sutures a surgeon prefers to place or on the particular type of intraocular surgery to be performed.

An alignment projection 23, as shown in FIG. 1, which could also be in the form of a planar mark or score line, extends from the second major surface 15 and is aligned with the central projection 16c, to help the surgeon in the proper placement of the marking device 10 on the eye. A similar purpose is served by an alignment notch 25 formed in the edge defined by the superior arc 20 of the marking device and aligned with projections 16c and 23. These placement aids are optional, since the marking device may still be used efficiently without them.

In the embodiment illustrated in FIGS. 1 and 2, the arcuate body member 12 is 11 mm long along the inferior arc 18, 5 mm wide and 2.5 mm thick. The projections 16a and 16b are 1 mm long, from 0.10 to 0.40 mm wide and extend 0.5 mm from the first major surface 14. The central projection 16c is 1.5 mm long, with the remaining dimensions the same as the other projections. The projections are equiangularly spaced 1.8 mm from each other on center at the superior arc of the first set 16a. The inferior arc of the second set 16b of projections is spaced 0.75 mm from the superior arc of the first set 16a of projections. It should be understood, however, that the dimensions and spacing of the projections 16 and the dimensions of the body member 12 may vary in order to accommodate the suture marking needs of a particular type of surgery without affecting the usefulness of the device 10.

As illustrated in FIG. 1, a handle 26 is attached to the second major surface 15 to facilitate better control of the marking device 10. One of ordinary skill in the art will understand that the handle may be permanently attached or removably attached by any suitable mechanical fastening means, such as threaded connection elements, bayonet connection elements, friction fit, etc. The removable attachment facilitates the interchangeability of body members 12 having varying radii of curvature or other dimensions or varying numbers or arrangements of projections 16.

Figure 3:
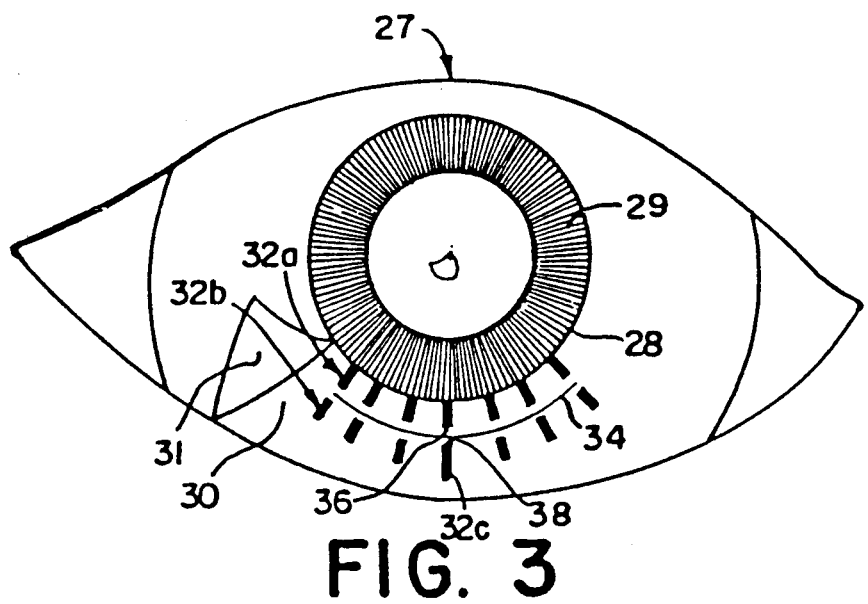
FIG. 3 is a diagrammatic elevational view of a patient's eye showing the ink markings transferred from the embodiment of the marker of the present invention illustrated in FIGS. 1 and 2.

Before describing the other preferred embodiments of the marking device according to the present invention illustrated in FIGS. 4 through 7, the method of using the above-described marking device in a typical surgical technique for performing a cataract extraction will be described with particular reference to FIG. 3, which illustrates, rather diagrammatically, an eye 27. Eye 27 includes a limbus 28 forming a border between the cornea 29 (including the iris) and the sclera 30.

A surgeon may first determine preoperative corneal astigmatism using a surgical keratometer (not shown). A central meridian is marked on the eye at the limbus with a 30 gauge needle dipped in methylene blue. This central mark allows for perfect centration of the marking device 10 with respect to the cornea. The placement of the device may, however, vary with the operative procedure.

The conjunctiva, a thin white membrane of tissue which covers the sclera and terminates at the limbus, is then reflected (pulled rearward) in order to expose the sclera. This is usually done by severing the conjunctiva at the limbus and pulling it rearward like a bedsheet, thus progressively detaching it from and exposing the sclera. This is illustrated schematically in FIG. 3 by reference numeral 31.

The tips of the projections 16 of the marking device 10 are then coated with a non-toxic, waterproof, absorbable ink or stain, such as gentian violet. This is conveniently done by pressing the projections 16 onto a marking pad soaked with gentian violet or any other suitable, non-toxic indelible or waterproof ink. It should be understood that any other means of coating the projections may be employed, for example, rubbing the projections with a surgical marking pencil (not shown) incorporating the ink. Although the ink is waterproof to be visible during the surgical procedure, gentian violet or other suitable inks fade gradually and disappear completely by the first postoperative day.

The inked marking device 10 is then aligned in proper position with the inferior arc 18 aligned with the limbus, and with the central projection 16c, the alignment projection 23 and/or the alignment notch 25 in alignment with the marking of the central meridian. Then the device is pressed gently against the eye 30, thus transferring the ink from the projections 16a, 16b and 16c onto the sclera and/or limbus to form corresponding ink marks 32a, 32b and 32c. The marking device 10 is then removed from the eye 27. Access is then gained into the anterior chamber of the eye to remove the cataract by means of an incision 34 made through the sclera and/or limbus following the contour of the ink marks. The placement of incision 34 relative to the ink marks can vary according to the surgeon's preference. For example, the incision could also be located along an arc formed by joining the superior ends 36 of the first set of marks 32a or the inferior ends 38 of the second set of marks 32b. The cataract extraction is then performed according to the surgeon's preference. The ink marks 32 remain visible throughout the entire cataract procedure. They act as a guide even if the situation warrants an enlargement of the incision. Importantly, the ink marks 32 serve as a guide for final suture placement, thus assuring that the sutures are properly radially placed.

Although suture placement varies by preference of the surgeon, one way to use the ink marks 32 to locate the sutures is to use the superior ends 36 of the first set of ink marks 32a to define the insertion points for the suture needle on one side of the incision line 34 and to use the inferior ends 38 of the second set of ink marks 32b to define the exit points for the suture needles on the opposite side of the incision line 34.

If a smaller incision is required, as in a phacoemulsification cataract operation, or a secondary lens implantation, the length of the incision can be adjusted and the same marking device 10 used.

This marking device 10 has proved to be a very valuable tool in all forms of cataract, primary intraocular lens, and secondary intraocular lens implant surgery.

Other preferred embodiments of marking devices according to the present invention will now be described with reference to FIGS. 4 through 7.

Figure 4:
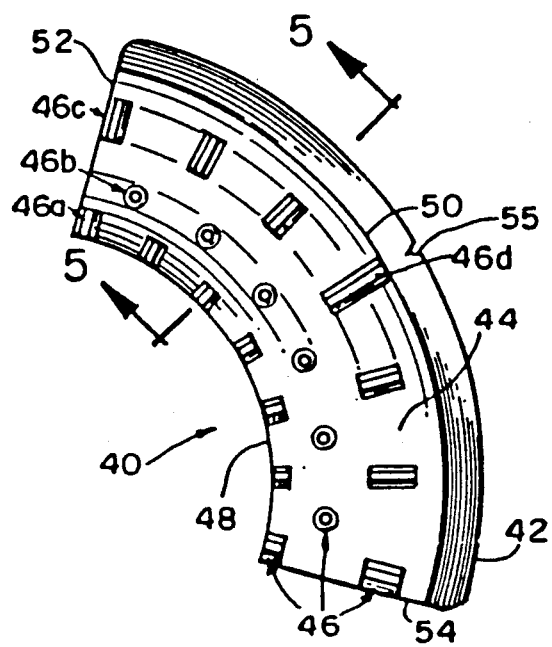
FIG. 4 is a side elevational view of a second embodiment of a marking device according to the present invention showing projections extending from a first, curvilinear major surface of the arcuate body member.
Figure 5:
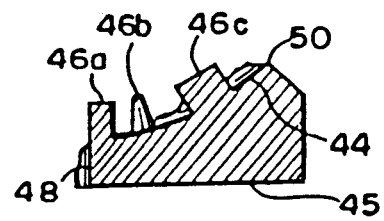
FIG. 5 is a cross-sectional view of the second embodiment of the marking device taken along the plane defined by lines 5—5 of FIG. 4.

Turning first to FIGS. 4 and 5, there is shown a marking device 40. The marking device has a generally arcuate body member 42 including a first major surface 44. As best seen in FIG. 5, the first major surface 44 is curvilinear in general, and concave, in particular. The concave surface 44 should have a radius approximating the radius of the eye, which may make it easier to mark the eye with marking device 40 than with marking device 10, although marking device 10, including a planar first major surface 14 has been found to be acceptable in actual practice.

A second major surface 45 is generally opposed to the first major surface 44. A handle (not shown) extends from the second major surface 45.

A plurality of projections 46 extend from the first major surface 44 and are arranged in three general sets, 46a, 46b and 46c. An elongated central projection 46d is illustrated as being part of the third set 46c. The projections of sets 46a and 46c are generally rectangular and are radially aligned with each other and equiangularly spaced along the length of the body member 42. Preferably, as illustrated in FIG. 4, the first set of projections 46a extends radially from an inferior arc 48 of the body member 42 toward a superior arc 50 of the body member 42. The projections are arranged along the body member 42 from one edge 52 to the opposite edge 54, which edges join the inferior and superior arcs 48 and 50.

The second or middle set of projections 46b are generally conical in shape, with the blunt tips of the cones being at the same height as the blunt tips of the first and third sets of projections 46a and 46c. The purpose of the second set of projections 46b is to more specifically define the location of an incision line between the other sets of projections which define the location of the sutures. As in the first embodiment of the present invention, the shape, dimensions and arrangement of the projections 46 may be varied as desired. For example, if desired, the second set of projections 46b, instead of being discrete points, could be joined together as a single, continuous raised projection to specifically mark an incision line. Likewise, the dimensions of the generally arcuate body member 42 may also be varied within reasonable limits.

If desired, an alignment projection (not shown) or other alignment mark (not shown) aligned with the central projection 46a could also extend from or be placed on the second major surface. An optional alignment notch 55 is formed in the superior arc 50 of the body member and aligned with the central projection 46d.

As presently preferred, the inferior arc 48 has a radius of about 6 mm, corresponding to the average radius of curvature of a patient's limbal or corneal radius of curvature. Each projection within first set 46a is 0.5 mm long and has a blunt tip about 0.25 mm in width. The center points of the projections forming the second set 46b are preferably aligned on a radius of curvature 1 mm from the superior edge of the projections of the first set 46a. The tips of the projections of set 46b have a diameter of 0.25 mm. The inferior ends of the projections of the third set 46c are spaced on a radius of curvature 1 mm from the center of the radius of curvature of the middle set of projections 46b. The projections of the third set 46c have a length of 1 mm, except for the central projection 46d, which has a length of 1.5 mm. All of the projections 46 extend 1 mm from the concave first major surface 44 of the body member 42.

The marking device 40 is used in the same general manner as described above with respect to the marking device 10. If it is desired to coat the blunt projections 46 with suitable ink from a marking pad, it should be clear that the marking pad should have a convex radius of curvature corresponding to the concave radius of curvature of the tips of the projections.

Figure 6:
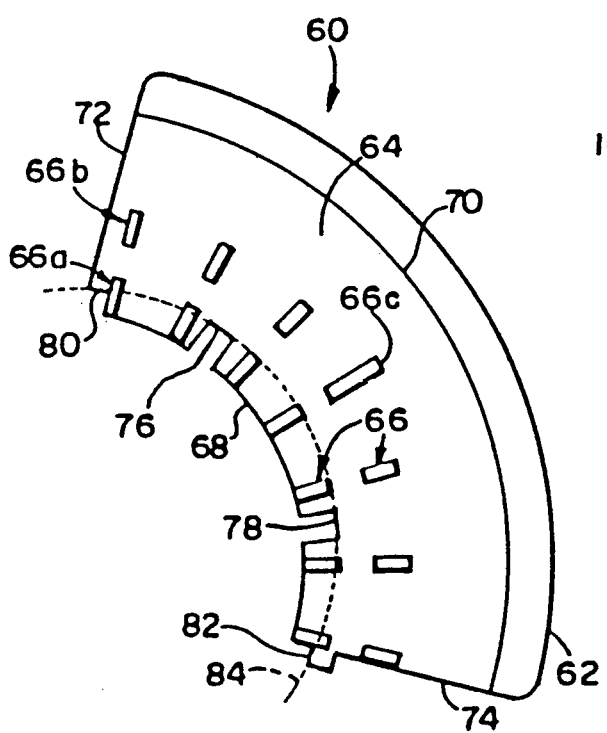
FIG. 6 is a general, diagrammatic side elevational view generally corresponding to FIGS. 2 and 4 of a third embodiment of a marking device according to present invention in which certain positioning means are used to position the marking device on a patient's eye.

A marking device 60 in accordance with a third embodiment of the present invention is illustrated schematically in FIG. 6. The marking device 60 includes an arcuate body member 62 having a first major surface 64 from which extend a plurality of projections 66 aligned in two sets, 66a and 66b, including a central projection 66c. The first major surface 64 of the body member 62 may be substantially planar as in the embodiment of FIGS. 1 and 2, or may be concave as in the embodiment of FIGS. 4 and 5.

The body member 62 includes an inferior arc 68 having a radius of curvature generally corresponding to the radius of curvature of the limbus. A superior arc 70 is opposite the inferior arc 68. The inferior and superior arcs are connected by edges 72 and 74. As with the other embodiments, the shape, dimensions and arrangement of the projections and the body member may be varied as desired depending on the procedure involved and the surgeon's preferences. The body member 62 may also include an alignment notch (not shown) or other alignment mark (not shown) aligned with the central projection 66c for the purpose described above with respect to the alignment projection 23 and the alignment notch 25 of the embodiment of FIGS. 1 and 2.

The embodiment of FIG. 6 differs from the other embodiments by including additional positioning means 76, 78, 80 and 82. These positioning means allow for the positioning of the marking device 60 in a proper location on the limbus, where the corneal end of the limbus is represented by the dash line 84. The positioning means 76 and 78 are in the form of apertures extending from the first major surface 64 through the second major surface (not shown) of the body member. The alignment along the limbus can be visually observed through the apertures 76 and 78 as the marking device 60 is being aligned to place the appropriate ink marks on the patient's eye.

Positioning means 80 may be deemed to be an aperture similar to apertures 76 and 78 in the nature of a notch formed in the corner of the body member 62 where the inferior arc 68 meets the edge 72. It can be seen in FIG. 6, that unlike the embodiments previously illustrated and described, the projections 66a and 66b closest to the edge 72 are spaced slightly from the edge 72, rather than being flush with the edge. A flange 82 extends from the opposite edge 74 and acts as a positioning means and may be used in conjunction with one or more of the other positioning means 76, 78 and 80. Although four positioning means are illustrated in the device 60 of FIG. 6, to obtain proper alignment of the device with respect to the limbus, it is only necessary to have two reference points along the radius of curvature of the limbus.

The marking device 60 of FIG. 6 is used in the same general manner set forth above with respect to the other embodiments of the present invention, except that surgeons may prefer to make the incision of a smaller radius through the corneal end of the limbus as illustrated by the line 84. The inferior edges of the projections 66a and the inferior edges of the projections 66b may be used as markers for positioning the sutures on opposite sides of the incision line. The marking device 60 is more adaptable to making an incision of a smaller radius than the marking device 10, which is well adapted for making an incision of a larger radius.

Figure 7:
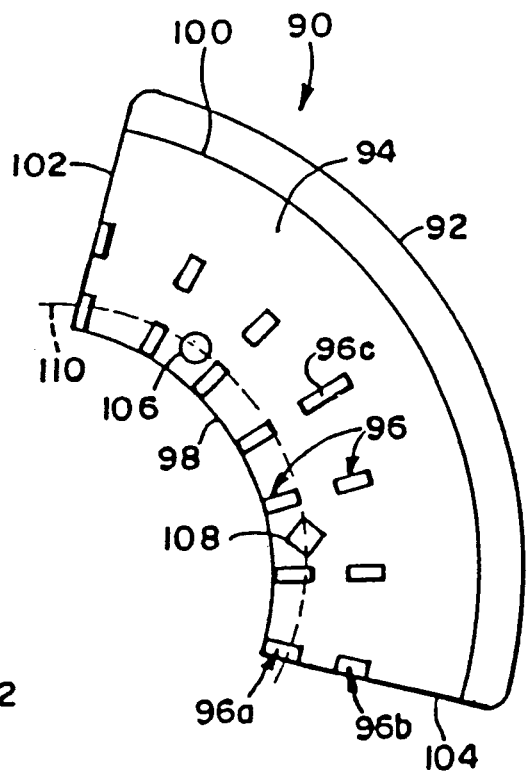
FIG. 7 is another general, diagrammatic side elevational view generally corresponding to FIGS. 2, 4 and 6 of a fourth embodiment of a marking device according to the present invention in which other types of positioning means are used to position the marking device on a patient's eye.

FIG. 7 illustrates diagrammatically in the same fashion as FIG. 6 another embodiment of a marking device 90 according to the present invention. The marking device 90 includes a generally arcuate body member 92 including a first major surface 94 which may be substantially planar or concave. Opposed to major surface 94 is the second major surface (not shown). A plurality of projections 96 extend from the first major surface 94 and are radially and equiangularly arranged and aligned in two sets 96a and 96b as illustrated. A central projection 96c makes a central mark on the eye. The body member 92 includes an inferior arc 98 and an opposed superior arc 100 and connecting edges 102 and 104. The body member 92 may also include a central alignment notch or mark as in the previously described embodiments.

The marking device 90 includes two positioning means 106 and 108 for positioning the marking device 90 on a patient's eye with respect to the corneal end of the limbus, represented by dash line 110. The positioning means of FIG. 7 comprise apertures 106 and 108 extending from the first major surface 94 through the body member 92 to the second major surface. In the embodiment illustrated in FIG. 7, aperture 106 is circular while aperture 108 has a diamond shape. It should be clear to those of ordinary skill in this technology that other shapes for the apertures may be used, just as other shapes, arrangements, etc. of the projections may also be used. As in the embodiment of FIG. 6, the marking device 90 of FIG. 7 is intended for use in making an incision of a smaller radius through the corneal end of the limbus as illustrated by the line 110.

The present invention may be embodied in other specific forms without departing from the spirit or essential attributes thereof and, accordingly, reference should be made to the appended claims, rather than to the foregoing specification as indicating the scope of the invention.

We claim:

1. A marking device for marking a sclera and/or limbal portion of an eye during intraocular surgery comprising a generally arcuate body member having opposed first and second major surfaces, the first major surface being substantially planar, a first set and a second set of plurality of projections extending from the first major surface, the first set of projections being generally equiangularly spaced from each other and radially arranged in a pattern along an arc of a circle, the second set of projections being radially aligned with and equidistically spaced from the first set of projections, the projections being adapted to be inked and to transfer to an eye the ink in markings corresponding to the projections so that incisions and sutures can be placed in the sclera and/or limbal portion of the eye relative to the markings to standardize and define incisions and suture placement with respect to the sclera and/or limbus.

2. A marking device according to claim 1 wherein the arcuate body member covers between 40 degrees and 160 degrees of a circle.

3. A marking device according to claim 2 wherein the arcuate body member covers approximately 90 degrees of a circle.

4. A marking device according to claim 2 wherein the arcuate body member further comprises an inferior arc and a superior arc, the inferior arc having a smaller radius than the superior arc and wherein the first set of projections extend from the inferior arc in a direction toward the superior arc.

5. A marking device according to claim 4 wherein the inferior and superior arcs are joined by end edges and wherein a projection is located adjacent each end edge of the arcuate body member along the inferior arc and the first set of a plurality of projections is located along the inferior arc between the projections adjacent the end edges.

6. A marking device according to claim 1 wherein the arcuate body member further comprises an inferior arc and a superior arc, the inferior arc having a smaller radius than the superior arc, the marking device further including a central projection distinct from and centrally located with respect to the other projections extending from the first major surface, and alignment means carried by the body member on a surface other than the first major surface and aligned with the central projection for aligning the marking device on the eye.

7. A marking device according to claim 6 wherein the alignment means is a notch formed in the superior arc.

8. A marking device according to claim 6 wherein the alignment means is a mark formed on the second major surface.

9. A marking device according to claim 1 further comprising at least two positioning means for positioning the marking device on the eye.

10. A marking device according to claim 9 wherein the positioning means are apertures extending from the first major surface through the arcuate body member to the second major surface.

11. A marking device according to claim 9 wherein the positioning means are flanges extending from and generally within the plane of the arcuate body member.

12. A marking device according to claim 9 wherein the positioning means are an aperture extending from the first major surface through the body member to the second major surface and a flange extending from and generally within the plane of the arcuate body member.

13. A marking device according to claim 1 having a handle extending from the second major surface.

14. A marking device for marking a sclera and/or limbal portion of an eye during intraocular surgery comprising a generally arcuate body member having opposed first and second major surfaces, the first major surface being concave, a plurality of projections extending from the first major surface, the projections being generally equiangularly spaced from each other and radially arranged in a pattern along an arc of a circle, the projections being adapted to be inked and to transfer to an eye the ink in markings corresponding to the projections so that incisions and sutures can be placed in the sclera and/or limbal portion of the eye relative to the markings to standardize and define incisions and suture placement with respect to the sclera and/or limbus.

15. A marking device according to claim 14 wherein the concave first major surface has a radius of curvature generally corresponding to the curvature of the eye.

16. The marking device according to claim 14 wherein the arcuate body member covers between 40 degrees and 160 degrees of a circle.

17. A marking device according to claim 16 wherein the arcuate body member covers approximately 90 degrees of a circle.

18. A marking device according to claim 14 wherein the arcuate body member further comprises an inferior arc and a superior arc, the inferior arc having a small radius than the superior arc and wherein the projections extend from the inferior arc in a direction toward the superior arc.

19. A marking device according to claim 16 wherein the inferior and superior arcs are joined by end edges and wherein a projection is located adjacent each end edge of the arcuate body member along the inferior arc and a first set of a plurality of projections is located along the inferior arc between the projections adjacent the end edges.

20. A marking device according to claim 19 having a second set of a plurality of projections radially aligned with and equidistantly spaced from the first set of projections.

21. A marking device according to claim 14 wherein the arcuate body member further comprises an inferior arc and a superior arc, the inferior arc having a smaller radius than the superior arc, the marking device further including a central projection distinct from and centrally located with respect to the other projections extending from the first major surface, and alignment means carried by the body member on a surface other than the first major surface and aligned with the central projection for aligning the marking device on the eye.

22. A marking device according to claim 21 wherein the alignment means is a notch formed in the superior arc.

23. A marking device according to claim 21 wherein the alignment means is a mark formed on the second major surface.

24. A marking device according to claim 14 further comprising at least two positioning means for positioning the marking device on the eye.

25. A marking device according to claim 24 wherein the positioning means are apertures extending from the first major surface through the arcuate body member to the second major surface.

26. A marking device according to claim 24 wherein the positioning means are flanges extending from and generally within the plane of the arcuate body member.

27. A marking device according to claim 24 wherein the positioning means are an aperture extending from the first major surface through the body member to the second major surface and a flange extending from and generally within the plane of the arcuate body member.

28. A marking device according to claim 14 having a handle extending from the second major surface.

* * * * *